United States Patent [19]

Sramek

[11] Patent Number: 4,871,529
[45] Date of Patent: Oct. 3, 1989

[54] AUTOPHOBIC SILICONE COPOLYOLS IN HAIRSPRAY COMPOSITIONS

[75] Inventor: John A. Sramek, County of Racine, Wis.

[73] Assignee: S. C. Johnson & Son, Inc., Racine, Wis.

[21] Appl. No.: 213,050

[22] Filed: Jun. 29, 1988

[51] Int. Cl.$^4$ .......................... A61K 7/11; A61K 7/06
[52] U.S. Cl. ...................................... 424/47; 424/71; 424/DIG. 1; 424/DIG. 2; 424/78
[58] Field of Search ............... 424/47, 71, 78, DIG. 1, 424/DIG. 2

[56] References Cited

U.S. PATENT DOCUMENTS

| | | | |
|---|---|---|---|
| 2,782,790 | 2/1957 | Hersh et al. | 132/203 |
| 3,246,048 | 4/1966 | Haluska | 528/27 |
| 3,364,246 | 1/1968 | Rossmy | 556/450 |
| 3,392,040 | 7/1968 | Kass | 106/287.13 |
| 3,505,377 | 4/1970 | Morehouse | 556/445 |
| 3,641,239 | 2/1972 | Mohrlock | 424/64 |
| 3,928,558 | 12/1975 | Cheesman et al. | 424/47 |
| 3,957,843 | 5/1976 | Bennett | 556/420 |
| 3,980,688 | 9/1976 | Litteral et al. | 556/446 |
| 4,136,250 | 1/1979 | Mueller et al. | 528/29 |
| 4,192,862 | 3/1980 | Pengilly | 424/47 |
| 4,243,657 | 1/1981 | Okumura et al. | 424/47 |
| 4,311,695 | 1/1982 | Starch | 514/63 |
| 4,364,837 | 12/1982 | Pader | 252/173 |
| 4,378,345 | 3/1983 | Okumura et al. | 424/45 |
| 4,387,090 | 6/1983 | Bolich | 424/70 |
| 4,423,032 | 12/1983 | Abe et al. | 424/70 |
| 4,423,041 | 12/1983 | Clum et al. | 514/772 |
| 4,450,152 | 5/1984 | Ona et al. | 424/70 |
| 4,543,249 | 9/1985 | Nelson | 424/70 |
| 4,563,347 | 1/1986 | Starch | 424/70 |
| 4,574,082 | 3/1986 | Tietjen et al. | 424/63 |
| 4,584,337 | 4/1986 | Lee et al. | 524/500 |
| 4,597,962 | 7/1986 | Grollier et al. | 424/47 |
| 4,597,964 | 7/1986 | Ziemelis et al. | 424/70 |
| 4,600,751 | 7/1986 | Lee et al. | 525/404 |
| 4,601,902 | 7/1986 | Fridd et al. | 424/70 |
| 4,657,959 | 4/1987 | Bryan et al. | 524/266 |

FOREIGN PATENT DOCUMENTS

116207 8/1984 European Pat. Off. .
802467 2/1957 United Kingdom .
1158139 10/1966 United Kingdom .

OTHER PUBLICATIONS

Datasheet, "Dow Corning ® 190 and 193 Surfactants," Dow Corning Corp., Midland, Mich., 3 pages, (1980).
Datasheet, "Dow Corning ® Q2-5220 Resin Modifier," Dow Corning Corp., Midland, Mich., Form No. 24-349-86, 2 pp., (1986).
"Structure/Property Relationships for Silicone Polyalkyleneoxide Copolymers and Their Effects on Performance in Cosmetics," S. C. Vick, *Soap/Cosmetics/Chemical Specialties*, vol. 60, p. 36ff, May., 1984.
Datasheet, "SIWET ™ Surface Active Copolymers," Union Carbide Corp., Danbury, Conn., No. F-47773, 12/80-5M, 22 pp. (1980).
Datasheet, "SIWET ™ Surfactants For Use in Personal Care Products," Union Carbide Corp., Danbury, Conn., No. SC-838, 10/87-2M, 1987, 4 pages, (1987).
Datasheet, "Dow Corning ® 244, 245, 344 and 345 Fluids; Dow Corning ® 200 Fluid, 0.65 cs," Dow Corning Corp., Midland, Mich., Form No. 22-904-82, 6 pages, (1982).
*The Chemistry and Manufacture of Cosmetics*, p. 1150.

*Primary Examiner*—Ellis P. Robinson
*Assistant Examiner*—Susan S. Rucker

[57] ABSTRACT

Disclosed in a hairspray composition in an ethanol solvent system possessing improved body as a result of the inclusion of an amount of an autophobic silicone copolyol which is effective to cause the hairspray resin composition to contract on the hair at between 20° C. and 37° C. The silicone copolyol is a polymer of organosiloxy units selected from the group consisting of dimethylsiloxy units, trimethylsiloxy units, $CH_3SiO(C_xH_{2x})(OCH_2CH_2)_y(OCHCH_3CH_2)_zOR$ and $(CH_3)_2SiO(C_xH_{2x})(OCH_2CH_2)_y(OCHCH_3CH_2)_zOR$ where x has a value of 1 to 12, R is hydrogen or alkyl of 1 to 4 carboxy atoms, y is greater than or equal to 1, z is greater than or equal to 0 and the sum of y+z and the amount of dimethylsiloxy units and trimethylsiloxy units is such that the silicone copolyol imparts an autophobic effect to the hairspray composition.

23 Claims, No Drawings

AUTOPHOBIC SILICONE COPOLYOLS IN HAIRSPRAY COMPOSITIONS

BACKGROUND OF THE INVENTION

1. Field of the Invention

This invention relates to ethanol solvent-based hairspray compositions which employ a specific type of silicone copolyol which causes the hairspray composition to contract upon drying and thereby improve the body and hair setting properties of the hairspray composition.

2. Description of the Prior Art

Various types of silicone materials, and more specifically silicone copolyols such as those designated by The Cosmetic, Toiletry and Fragrance Association ("CTFA") name of "dimethicone copolyols", have been suggested for use in hairspray compositions to modify the properties of the compositions to leave the hair with various properties such as ease of brushing, to give the hair a softer feel, to reduce tackification after spraying or to impart luster to the hair.

For example, DOW CORNING ® 190 and 193 Surfactants are water soluble silicone glycol copolymers which are said to be useful in hairspray products to impart luster, detackification and hold properties in hairspray compositions when used at 0.1 to 1% of the composition. DOW CORNING ® Q2-5220 Resin Modifier is said to be a dimethicone copolyol as a resin modifier for hairsprays, mousses, setting lotions and styling gels which is readily compatible with ethanol and water. At a use level of 0.1 to 1.0%, the DOW CORNING Q2-5220 Resin Modifier is said to plasticize resins, making them softer, more flexible and less tacky.

European Pat. Appln. No 116,207 to Elliott et al. teaches an aerosol hairspray formulation comprising a hair-holding resin dissolved in a solvent system such as ethanol, and aerosol propellant and from 0.5 to 10% by weight of the formulation of at least one cyclic silicone such as dimethylsiloxane cyclic tetramer or dimethylsiloxane cyclic pentamer in addition to the dimethicone copolyol such as DOW CORNING 193 surfactant.

The examples in the Elliott et al. Patent indicate that the dimethylsiloxane cyclic tetramer or pentamer is used in amounts equal to or in excess of 10 parts of the tetramer or pentamer to 1 part of dimethicone copolyol. Linear and cyclic polydimethylsiloxanes are known to be hydrophobic and are therefore not compatible with water. Dimethicone copolyol such as DOW CORNING Q2-5220 resin modifier tend to form uniform films when compositions containing the silicone and a hairspray resin dissolved in an ethanol solvent system are sprayed out on a substrate such as a glass slide or the hair. Introduction of a hydrophobic silicone such as a dimethylsiloxane cyclic pentamer causes the film to contract toward the center of the substrate as the composition dries. The combination of the dimethicone copolyol and dimethylsiloxane cyclic pentamer which results in a film that contracts upon drying is thus said to impart an "autophobic" effect on the hairspray composition.

A number of hair spray compositions are commercially available and have been marketed for a number of years which contain dimethicone copolyol and also which contain dimethicone copolyol and cyclomethicone as stated on the package label of the product. For example, FINESSE pump and FINESSE Aerosol hairspray formulations sold by Helene Curtis Industries, Inc. list both dimethicone copolypol and cyclomethicone on their label. The product, when sprayed on a glass slide, was noted to have an autophobic effect in that the composition tended to contract towards the center of the glass slide upon drying. The FINESSE hairsprays were based on an ethanol solvent system.

The Elliott et al. patent application discusses the disadvantages of only using a dimethicone copolyol such as DOW CORNING 193 surfactant in hairspray compositions and suggest the use of dimethylsiloxane cyclic tetramer or pentamer in such such compositions, presumably to obtain this autophobic effect. A rather significant level of dimethylsiloxane cyclic tetramer or pentamer must be used to overcome the natural tendency of dimethicone copolyols that are water soluble to form an evenly spread film upon drying. The autophobic effect of this combination of silicone materials can be used to improve the body of hair sprayed with the hairspray resin since the hairspray resin tends to contract as it dries and thus adheres the fibers of the hair together at the points where one strand crosses another.

The use of dimethicone copolyols in cosmetic and personal care formulations is discussed in a paper by F. C. Vick in *Soap/Cosmetics/Chemical Specialties* for May, 1984, Vol. 60. p. 36ff entitled "Structure/property Relationships for Silicone Polyalkyleneoxide Copolymer and Their Effects or Performance in Cosmetics." The composition of the copolymers discussed very widely in molecular weight and the content and type of alkyleneoxy block present, i.e., ethyleneoxy or propyleneoxy units, present in the copolymers discussed. However, the dimethicone copolyols described in this paper have a 0.1% cloud point of at least 41° C. or more which indicates that these silicone dimethicone copolyols are rather water soluble.

Union Carbide Corporation also markets a series of dimethicone copolyols under the trademark SILWET. The Union Carbide Data Sheet No. F-44773 12/80-5M entitled "SILWET ® Surface Active Copolymers", 1980. page 13 suggests the use of SILWET copolymers L-720, L-7600 and L-7002 for use in personal care products, specifically for hair care products. Nothing is mentioned concerning the use of SILWET ® L-7602 in hair care applications. A 1987 Union Carbide Data Sheet entitled "SILWET ® SURFACTANTS FOR USE IN PERSONAL CARE PRODUCTS" lists SILWET L-7602 among 5 others for personal care use, some of which included improving hair sheen and soft feel. The recommended starting use level is 1.0% by weight of the total formulation.

U.S. Pat. No. 3,928,558 to Cheesman et al. teaches that certain polydimethylsiloxane-polyoxyalkylene block copolymers can be incorporated into hairspray compositions comprising a film forming resin in a cosmetic vehicle. These polymers have a ,silicon content of 15 to 25%, a molecular weight of from,1,200 to 5,000 and a viscosity at 25° C. of 3 to 10 poises and their inclusion makes the resin easier to brush out from the hair. Cheesman et al. teach that all three variables are critical in obtaining the proper polydimethylsiloxane-polyoxyalkylene block copolymers which can be used in their invention. Cheesman et al. teaches nothing concerning the presence or absence of an autophobic character to the block copolymers employed in their invention.

U.S. Pat. No. 4,423,041 to Clum et al. teaches detackifying compositions for use in emulsion-type personal care compositions which comprise a mixture of a silicone fluid which can be a dimethylsiloxane cyclic tetramer or pentamer (CTFA name "Cyclomethicone") and a silicone wax in a ratio of from about 9:1 to 1:3. The silicone wax can be a dimethicone copolyol having a molecular weight of about 1,600 to about 2.000. but is required to be a solid or semi-solid at body temperature and must be insoluble in water and insoluble or only slightly soluble in cosmetic oils. Nothing is taught concerning the use of this combination of materials in a hairspray composition.

SUMMARY OF THE INVENTION

What the prior art has failed to recognize is that SILWET ® L-7602 surfactant--which contains a relatively high amount of hydrophobic dimethylsiloxane units relative to the siloxane units containing the hydrophilic polyethyleneoxide units—imparts autophobic properties to ethanolic solvent system hairspray compositions without a necessity for the use of large amounts of hydrophobic silicone compounds or polymers as will be further described below. The unique properties of the class of autophobic silicone copolyols to which SILWET ® L-7602 belongs provide significant advantages when such compounds are incorporated into hairspray compositions based on ethanol solvent systems.

The present invention provides a hairspray composition—in the form of a pump spray or a self-pressurized aerosol composition--having improved body by virtue of the presence of a sufficient, but small, amount of an autophobic silicone copolyol surfactant to cause the hairspray film to contract on the hair at between 20° C. and 37° C. rather than to spread into an even film upon drying.

These compositions possess improved hair body properties through the use of a single silicone copolyol surfactant which is a specific type of dimethicone copolyol which is used in an amount which is effective to impart autophobic properties to a hairspray composition using an ethanol soluble hairspray resin dissolved in an ethanol solvent system which can optionally further contain an aerosol propellant. Generally, the autophobic silicone copolyol is used in an amount of 0.02% to about 0.5% weight percent based on the total weight of the hairspray composition with the objective being to use the minimum level needed to achieve the desired body and other properties on the hair sprayed with the composition. More preferably, the amount of autophobic silicone copolyol employed is about 0.05% to 0.2% of the hairspray composition.

Another advantage of the use of such an autophobic silicone copolyol surfactant is that only a small amount of such a surfactant is necessary to obtain a hairspray composition which is autophobic upon drying. This has the advantage of minimizing the use of silicone surfactants in the composition while permitting the properties of the silicone such as softer hair feel and reduced stickiness of the sprayed hair to be observed. There is no need to employ a rather large amount of hydrophobic silicone material such as decamethyl cyclopentasiloxane relative to the dimethicone copolyol to overcome the film spreading nature of the latter and thereby obtain a hairspray composition which is autophobic upon drying.

The use of small amounts of silicone additives is also advantageous from an economic standpoint since silicone materials are rather expensive. It is also well known that use of an excess of silicone additive can result in loss of adhesion and hold in the hair. Furthermore, use of an excess amount of silicone additive can result in a hairspray composition that is too easy to brush out and is thus subject to loss of "body". For the purposes of this invention, the term "body" means "flexible hold" which is the ability of the hair to retain its styled appearance despite the effects of the wind or motion of the head on the hair.

The autophobic effect on the hairspray composition as it is drying on the hair causes large droplets of the composition to form and thus larger juncture points between hair fibers are produced. The result is stronger bonds and greater hold. This development is at the cost of less uniform coating of the hair by the hairspray resin. The effect of a non-uniform coating is that the hair fiber between the juncture points is more flexible and the styled hair feels softer to the touch. The end result is softer hair that holds better and thus has improved body. Another advantage of the use of small amounts of such autophobic silicone copolyols is that wicking forces are reduced which result in less matting of adjacent hair fibers. The benefits outweight the minor detrimental effects caused by such silicones: slower drying hairspray compositions and a slightly rougher hair surface that combs more raspy than a hairspray composition that leaves a more uniform film of resin on the hair.

In an alternative embodiment, the hairspray compositions of the present invention can additionally include further amounts of a hydrophobic silicone compound or polymer such as dimethylsiloxane cyclic pentamer, dimethylsiloxane cyclic tetramer or a low viscosity polydimethylsiloxane fluid of about 20, and preferably no more than about 10, centistokes in viscosity at 25° C., and mixtures thereof in an amount of about 0.02% to 0.5% by weight of the total hairspray composition. More preferably, the ratio of the autophobic silicone copolyol used herein and such hydrophobic silicone compound or polymer is 1:1 and the total of both additives is about 0.1% to 0.2% by weight of the hairspray composition.

DETAILED DESCRIPTION OF PRESENT INVENTION

These and other advantages of the present invention are provided by an aerosol hairspray composition having improved hold consisting essentially of from 0.5% to 8.0% by weight of an ethanol soluble hairspray resin dissolved in a sufficient amount of an ethanol solvent system to render the composition sprayable in aerosol form, said composition further containing an effective amount of an autophobic silicone copolyol to cause the sprayed film to contract on the hair at between 20° C. to 37° C. rather than to spread into an even film upon drying, said silicone copolyol surfactant consisting essentially of organosiloxy units selected from the group consisting of dimethylsiloxy units, $CH_3SiO(C_xH_{2x})(OCH_2CH_2)_y$ $(OCHCH_3CH_2)_zOR$, $(CH_3)_2SiO(C_xH_{2x})$ $(OCH_2CH_2)_y(OCHCH_3CH_2)_zOR$. and trimethylsiloxy units, and having a number average molecular weight of about 1500 to 6000 wherein x has a value of from 1 to 12, R is hydrogen or alkyl of 1 to 4 carbon atoms, y is greater than or equal to 1 and z is greater than or equal to 0 and the sum of y+z and the amount of dimethylsiloxy units and trimethylsiloxy units present is such that the silicone copolyol causes an ethanolic solution of the hairspray resin to contract on the hair rather to spread into an even film at 20° C. to 37° C. upon drying and a 1% by weight solution of the silicone copolyol in water has a cloud point of less than 30° C. and said ethanol solvent system consists essentially of a least 70% by weight of ethanol and any remaining solvent is selected from the group consisting of water, $R^1OH$ where $R^1$ is an alkyl of 3 or 4 carbon atoms, and mixtures thereof.

"Ethanol soluble hairspray resin" as used herein and in the attached claims is intended to mean a film-forming polymer which is soluble in an ethanol solvent system which is composed of at least 70% by weight of ethanol with any remaining solvent being selected from water, alcohols of the formula $R^1OH$ where $R^1$ is an alkyl of 3 or 4 carbon atoms such as isopropanol and tertiary-butanol and mixtures thereof with ethanol and isopropanol being most preferred. It is generally advisable to use the minimum amount of water since water tends to release the curls in the hair. Generally, less than 10% of the solvent system is water. Hairspray compositions may also contain small amounts of other solvents which do not provide the hairspray with an odor. Thus, less than 30% of other types of solvents such as methoxyethanol and 2-ethoxyethanol can also be included as a part of the aforementioned remainder of the ethanol solvent system.

The hairspray resins employed in the compositions of the present invention should be capable of forming a film and holding the hair of the user in place after evaporation of the volatile components of the hairspray composition. Hairspray resins are well known articles of commerce and many such resinous polymers are available commercially which contain radicals which render the polymers cationic, anionic, amphoteric or nonionic in nature. To provide optimum sprayability, the polymers employed in hairspray compositions typically range in number average molecular weight of from about 5,000 to about 100,000 with about 10,000 to 50,000 being more preferred For pump spray use, hairspray resins in the range of number average molecular weights in the range of about 10,000 to 50,000 are typically employed. The aerosol hair spray compositions of the present invention can utilize from 0.5% to 8% by weight of the total hair spray composition with 0.5% to 6% by weight resin nonvolatile solids content being preferred when the hairspray resin is in the form of a self-propelled hairspray composition using an aerosol propellent. If the nonvolatile resin solids content of the hairspray composition is kept low through the use of a sufficient amount of solvent, e.g., from 0.5 to about 3% by weight, higher molecular weight hairspray resin polymers in excess of a number average molecular weight of about 100,000 can be sprayed.

Examples of anionic hairspray resins are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride (molar ratio about 1:1) wherein such copolymers are 50% esterified with a saturated aliphatic alcohol containing from 1 to 4 carbon atoms such as ethanol or butanol; and acrylic copolymers and terpolymers containing acrylic acid or methacrylic acid as the anionic radical containing moiety such as terpolymers of methacrylic acid, butyl acrylate and ethyl methacrylate which is a presently preferred acrylic polymer. Another example of an acrylic polymer which can be employed in the compositions of the present invention is a polymer of tertiary-butyl acrylamide acrylic acid and ethyl acrylate which is commercially sold by BASF Corp. under the name BASF ULTRAHOLD 8 (CTFA - Cosmetic, Toiletry and Fragrance Association, designation: Acrylate/Acrylamide Copolymer). Such anionic hair setting and hairspray polymers are known in the art as can be seen from an examination of U.S, Pat. Nos. 3.405 084 to Bohac et al.; 3,577,517 to Kubot et al.; 3,577,518 to Shephard et al.; 3,927,199 to Micchelli; 4,192,861 to Micchelli et al.; 4,192 862 to pengilly et al.; 3,928,558 to Cheesman et al.; and 4,240,450 to Grollier et al. which are hereby incorporated by reference to teach such polymers.

Amphoteric polymers which can contain cationic radicals derived from monomers such as t-butyl aminoethyl methacrylate as well as carboxyl radicals derived from monomers such as acrylic acid or methacrylic acid can also be used in the compositions of the present invention. One example of an amphoteric polymer which can be used in the present invention is a polymer sold under the trademark AMPHOMER by National Starch and Chemical Corporation which has the CTFA name of Octylacrylamide/Acrylates/Butylaminoethyl Methacrylate Copolymer and is described in U.S. Pat. No. 4,192,861 as being a polymer of N-tert-octyl acrylamide, methyl methacrylate, hydroxypropyl methacrylate., acrylic acid and t-butyl aminoethyl methacrylate. Examples of such polymers are found in U.S. Pat. Nos. 3,726,288 to Nowak et al.; 3,981,987 to Link et al.; 4,237,253 to Jacquet et al.; and 4,358,567 to Hayama et al. which are hereby incorporated by reference to teach such polymers.

Examples of nonionic hairspray resins are homopolymers of N-vinylpyrrolidone and copolymers N-vinylpyrrolidone with compatible nonionic monomers such as vinylacetate and terpolymers of ethylacrylate, butylmethacrylate and methylmethacrylate. Nonionic polymers based on N-vinylpyrrolidone are commercially available from GAF Corp. N-vinylpyrrolidone containing hairspray resins are taught in U.S. Pat No 3,914,403 to Valan.

Examples of cationic hairspray resins are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate. Cationic polymers containing N-vinylpyrrolidone are commercially available from GAF Corp. such as those sold under the tradename Copolymer 937.

As is known in the art, copolymers which contain acetic groups and are water insoluble are usually used in their neutralized water-soluble form. Suitable neutralizing agents which may be included in the hairspray compositions of the present invention are amines, especially amino alcohols, preferably 2-amino-2-methyl-1,3-propanediol and 2-amino-2-methyl-1-propanol (CTFA name is Aminomethyl propanol). Similarly, amine containing hair fixative polymers can be used in their acid salt form if it is desired to render them more water soluble.

Hairspray compositions of the present invention can be dispensed from containers which are propellent-charged aerosol containers or pump spray containers. These containers are well known to those skilled in the art and are commercially available for various manufacturers such as American National Can Corp. and Continental Can Corp. No further discussion of the nature of these types of well known containers is deemed necessary since the present invention relates to a composition to be dispensed from such a container selected by the user.

When the hairspray compositions are to be dispensed from pressurized aerosol container, a propellent which may consist of 1 or more aerosol type propellent compounds may be used to propel the compositions to the air. The aerosol propellent may be mixed the composition and can comprise from 10 to 80% by weight of the total hairspray composition. More preferably, between 20 and 50% of a volatile hydrocarbon propellent of the type commonly used in hairspray compositions is employed which can include liquified lower hydrocarbons of 3 to 4 carbon atoms such as propane, n-butane and isobutane. Examples of other propellents which can be employed are low boiling chlorofluoro hydrocarbons such as trichlorofluoromethane, dichlorofluoromethane, and 1.2-dichloro-1,1.2,2-tetrafluoro ethane and mixtures thereof. Other examples of propellents are dimethylether, nitrogen and carbon dioxide. For ecological reasons, hydrocarbon propellents are generally preferred over chlorofluorohydrocarbons.

Alternatively, pressurized aerosol containers can be used where the propellent is separated from contact with the hairspray composition such as a two compartment can of the type sold under the tradename SEPRO from American National Can Corp.

Having discussed the conventional ingredients typically used in hairspray compositions, the autophobic silicone copolyols which provide the advance in the art made by the present invention will now be discussed.

The term "autophobic effect" is meant to mean that the silicone copolyol has a sufficiently hydrophobic character to cause a newly sprayed film of the hairspray composition to contact within a period of about 1 minute toward the center of the substrate so that at least about ½ of the sprayed film resides in the center of the substrate after the film is dried at between room temperature and body temperature. More preferably, at least ¾ of the film has contracted into the center of the substrate after the film is dried. This test can conveniently be run using a clean 1" by 3" glass slide wherein an even film of the hairspray composition is sprayed or evenly spread over the surface of the glass slide and the character of the film upon drying is observed. A silicone copolyol having surfactant properties is necessary for this effect and the hydrophobic character, i.e., the content of dimethylsiloxy units and trimethylsiloxy units present outweighs the hydrophilic character provided by the polyalkylene oxide radical containing siloxane units present in the silicone copolyol. There must be a balance between the hydrophobic and hydrophilic portions of the copolyol so that the copolyol has sufficient solubility in the ethanol as well as hydrophobic character to act as a surfactant. The molecular weight of the silicone copolyol must be sufficiently low that it is reasonably soluble in ethanol and must be high enough to provide sufficient hydrophobic character to act as a surfactant. A molecular weight of between about 1500 and 6000 is believed to be adequate to meet these needs.

With these properties in mind, the present invention relates to a hairspray composition containing a sufficient amount of an autophobic silicone copolyol to cause the sprayed film to contact on the hair at between 20° C. and 37° C. (which can be shown by the above glass slide test) rather than to spread into an even film upon drying. The silicone copolyol consists essentially of organosiloxy units selected from the group consisting of dimethylsiloxy units, $CH_3SiO(C_xH_{2x})(OCH_2CH_2)_y(OCHCH_3CH_2)_zOR$, $(CH_3)_2SiO(C_xH_{2x})(OCH_2CH_2)_y(OCHCH_3CH_2)_zOR$ and trimethylmethylsiloxy units which has a number average molecular weight of about 1500 to 6000 wherein x has a value of from 1 to 12, R is hydrogen or alkyl of 1 to 4 carbon atoms, y is greater than or equal to 1 and z is greater than or equal to 0 and the sum of y + z and the amount of dimethylsiloxy units and trimethylsiloxy units present is such that the silicone copolyol causes an ethanolic solution of the hairspray resin to contract on the hair rather than spread into an even film at 20° C. to 37° C. upon drying. Thus R can be hydrogen, methyl, ethyl, n-propyl, isopropyl, n-butyl, or tertiary butyl. preferably, R is hydrogen or methyl. For reasons of commercial availability x preferably has a value of 3 or 4. The silicon content is at least 10% by weight and preferably is between 15 and 30%. Preferably, y has a value of at least about 5. Introduction of hydrophobic propyleneoxy units, i.e. where z is greater than 0, can introduce some hydrophobic character into the polyalkylene oxide side chains. This can further, affect the autophobic character of the silicone copolyol. Preferably, z is 0 and the side chains are polyethylene oxide units capped by a hydrogen or a methyl radical. The hydrophobic character of the silicone copolymer is further defined by the requirement that a 0.1% by weight solution of the silicone copolyol in water have a cloud point of less than 30° C. and more preferably, that the cloud point be less than about 10° C. The cloud point determination is a standard test used to check the hydrophilicity of compounds and polymers.

One example of an autophobic silicone copolyol which has been found useful in the compositions of the present invention is a silicone copolyol sold by Union Carbide Corp. under the tradename SILWET L-7602 which is believed to be a trimethylsiloxy unit endblocked polymer composed of dimethylsiloxy units and $CH_3SiO(C_3H_6)$ $(OCH_2CH_2)_yOCH_3$ units which has a silicon content of about 16% by weight, a number average molecular weight of about 1,700 (the manufacturer reports a molecular weight of about 3000), a density of 1.027 and a viscosity at 25° C. of from about 70 to 130 centistokes. This silicone copolyol is the presently preferred silicone copolyol.

Another example of silicone polyol which has been found to have an autophobic character when it is added to an ethanolic solution of a hairspray resin is DOW CORNING® Q4-3667 which has a molecular weight of about 2400 (about 14% silicon content) and is composed of an average of about 10 dimethylsiloxy units endblocked with $(CH_3)_2Si(C_3H_6)(OCH_2CH_2)_xOH$ units where the total value of x in both endblocking units is 26 according to U.S. Pat. No. 4,136,250 to Mueller et al.

Other types of silicone copolyols can be identified by adding the amount of silicone copolyol to be used in the formulation. e.g., about 0.1 to 0.2% by weight, to a solution of a hairspray resin composition in ethanol and observing the effect of this silicone copolyol on the hairspray composition using the above mentioned glass slide test. Generally, the method of manufacturing silicone copolyols is well known in the art and a number of such copolyols are available commercially as noted above. The literature also contains a number of references to silicone copolyols and the manufacture such as the article by S. C. Vick noted previously, and U.S. Pat. Nos. 3,246,048 to Haluska; 3,505,377 to Morehouse; and 3,957,843 to Bennett; 3,980,688 to Litteral et al. Accordingly, one skilled in the art can select other suitable silicone copolyols for use in the present invention.

The amount of silicone copolyol included in that amount which is effective to cause the sprayed film to contact on the hair at between 20° C. to 37° C. rather than to spread into an even film upon drying. As noted above, the minimum amount of silicone which is effective to produce the autophobic effect in the hairspray composition and impart improved hold to the hair is employed. Use of excessive silicone copolyol can have detrimental effects on the hold properties of the hairspray resin since the silicone copolyols employed in this invention have a significant degree of silicone content and these silicone copolyols are not volatile. They therefore remain in the film of the hair spray resin and continue to affect its properties unlike volatile silicone fluids such as octamethyl cyclotetrasiloxane which evaporates along with the solvent upon drying. Generally, an effective amount is typically between 0.02 to 0.5% by weight of the total hairspray composition. More preferably, the amount of silicone copolyol present is between about 0.1% and 0.2% of the total composition.

The autophobic effects of the silicone copolyol can be further enhanced by the further inclusion of a volatile silicone fluid which can be a cyclic silicone fluid of the formula $[(CH_3)_2SiO]_n$ where n has an average value of about 4 (octamethyl cyclotetrasiloxane) to about 5 (decamethyl cyclopentasiloxane). As is well known, commercially available cyclic fluid are typically mixtures of cyclic siloxanes which contain from about 3 to about 8 silicons per molecule. Thus, the average value of the cyclic silicone fluid is one wherein n ranges between about 4 and 5 because of the presence of such other cyclic siloxanes.

Another example of a volatile silicone fluid is a linear silicone polymer fluid having the formula $(CH_3)_3SiO[(CH_3)_2SiO]_qSi(CH_3)_3$ where q has an average value such that the viscosity of the silicone fluid is no more than about 20 centistokes at 25° C. and more preferably, 10 centistokes at 25° C. The amount of such additional volatile silicone fluids included is an amount which is effective to enhance the autophobic character of the hairspray composition produced by the silicone copolyol. Typically, when a combination of autophobic silicone copolyol and volatile silicone fluid is employed, the total amount of silicone copolyol and volatile silicone fluid (cyclic silicone fluid, linear silicone polymer fluid, or mixtures thereof) is from about 0.02% to about 0.5 weight percent of the total composition. More preferably, the total amount of silicone copolyol and volatile silicone fluid is from about 0.1 to 0.2% by weight of the composition. More preferably, the ratio of silicone copolyol to volatile silicone fluid is 1:1 by weight.

The hairspray compositions are prepared in a conventional fashion. If a neutralizing agent is to be used, it is dissolved in the solvent and the resin is then added and mixed until a homogeneous solution is obtained. Alternatively, the resin can be dissolved in the solvent if it is sufficiently soluble to be dispersed without neutralization and then the neutralizing agents can be added. Otherwise, the resin is simply dissolved in the solvent and thereafter the silicone copolyol and any additional volatile silicone fluid can be added followed by any additional optional additives to modify the properties of the composition such as perfumes; plasticizers such glycols, phthalate esters and glycerine; emollients; lubricants and penetrants such as lanolin compounds; protein hydrolyzates and other protein derivatives; dyes, tints and other colorants; thickeners, anti-corrosion agents; Panthenol, preservatives and the like. The order of addition of such optional ingredients is generally not critical.

Hairspray compositions of the present invention can also employ a long chain amine neutralizing agent such as lauramidopropyl dimethylamine if the hairspray resin contains carboxyl groups as is described in my co-pending patent application, U.S. Ser. No. 07/213,566, entitled "Hairspray With Improved Adhesion/Removability Upon Washing", which was filed in the U.S. Patent Office on June 23, 1988 and is assigned to the same assignee as the present invention. In accordance with my co-pending application, up to 40% of the carboxyl radicals present in the resin which are to be neutralized are neutralized with a long chain amine such as lauramidopropyl dimethylamine and the remainder of the carboxyl radicals to be neutralized are then neutralized with another water soluble amine such as aminomethyl propanol. Hairspray compositions possessing improved adhesion for the hair can be obtained through the use of such long chain amine neutralizing agents.

After the composition is prepared, it is then packaged in a pump spray container if a non-pressurized aerosol product is desired. Otherwise, the composition is charged into a suitable pressurizable container which is sealed and then charged with a suitable propellent according to conventional techniques such as by adding a liquified propellent to the contents of the container under pressure. It is preferable to have all of the components of the hairspray composition mixed and homogeneous prior to the addition of the propellants. As noted above, a pressurized aerosol spray container of the type sold under the tradename SEPRO from American National Can Corp. can be used.

The resulting hairspray compositions exhibit improved body and a softer feel to the hair when sprayed on styled hair.

The following examples are provided to show various aspects of the present invention without departing from the scope and spirit of the invention. Unless otherwise indicated, all parts and percentages used in the Examples are by weight. In the following Examples, several tests were used to evaluate the compositions and, in some cases, their effect on the hair. They were done as follows:

Glass Slide Test: The autophobic character of hairspray compositions was evaluated by spraying the composition or spreading the composition from a pipette onto a clean 1"×3" glass microscope slide until a uniform film was obtained. The test done at room temperature (about 21° C. to 22° C.). The composition was then allowed to air dry and the appearance of the film upon drying was noted. A sample was considered to be autophobic if at least ⅓ of the film on the glass slide was pulled into the center of the glass slide so that the dried film area was at least about ½ of the total area of the glass slide.

Cloud point: The temperature at which a 0.1% by weight solution of the material to be tested in water changes from a clear solution to a hazy solution. This is sometimes called the "Inverse Solubility point."

Knot Adhesion test: In this test, the adhesion of individual strands of hair taken from the same hair swatch were measured. Individual strands of virgin hair were taken from the same swatch and a single loop knot was made in each strand of hair by twisting the strand into a loop and passing one end of the strand through the loop and pulling the ends until a loop approximately 1.5 cm in diameter was formed. 0.075 microliters of the product to be tested was then placed on the junction of each loop. i.e., at the point where the strand of hair overlaps to form the knot. Each looped strand containing the composition to be tested was then allowed to dry in an environmental chamber at a relative humidity of 38% and a temperature of 22 to 23° C. and were left in the chamber for a minimum of 1 hour to "condition" the strands. After such conditioning, the loop on the opposite side of the knot junction was cut and each of the non-looped ends was placed on the holder clip of an Instron testing machine, Model No. 4201 from Instron Corporation. The holder clips on the crosshead of the Instron machine were spread apart at a constant rate of 60 millimeters per minute and the test was deemed finished when the junction of the knot was broken. The response to the break was measured in "grams at break". The sampling rate during the test was 20 data points per second—measured electronically. A series of 20 individual strands was done for each test and the average value of the "grams at break" was reported as the Knot Adhesion value. A "Significance Level" letter of "A", "B" or "C" is also reported for each adhesion value. On a statistical basis, adhesion values having the same letter are statistically the same while adhesion values having different significance letters are statistically significantly different from each other regardless of the numerical values of adhesion reported.

The following materials were used in the Examples:

Absolute Ethanol was 200 proof SDA 40-2 ethanol

Acrylic polymer A was a terpolymer of 31% methacrylic acid. 42% butyl acrylate, and 27% ethyl methacrylate made by an aqueous emulsion polymerization process wherein the resulting resin had (via a gel permeation chromatographic technique) a number average molecular weight ("$M_n$") of 73,600, a weight average molecular weight ("$M_w$") of 183,000 and a sedimentation average molecular weight ("$M_z$") of 312,000 where $M_z$ is defined in U.S. Pat. No. 4,529,787 to Schmidt et al. and the product used was in the form of an aqueous emulsion at 40% nonvolatile solids content.

Acrylic polymer B was an aqueous emulsion polymer of the same composition and nonvolatile solids content as Acrylic polymer A, but the resin had a $M_n$ of 20.090, $M_w$ of 126,510 and $M_z$ of 276,330.

Acrylic polymer C was an aqueous emulsion polymer of the same composition and nonvolatile solids content as Acrylic polymer B. but was a higher molecular weight version of that resin that had a $M_n$ of 30,630, $M_w$ of 760.970 and $M_z$ of 1,929,230.

Acrylic polymer D Was a different batch of an aqueous emulsion polymer of the same composition and nonvolatile solids content as Acrylic polymer C.

AMP-95 was aminomethyl propanol (95%) from International Minerals & Chemicals Corp., equiv. weight =94.

Dimethicone Copolyol referred to below is a trimethylsiloxy-endblocked polymer of dimethyl siloxy units and $(CH_3)SiO(C_xH_{2x})(OCH_2CH_2)_zOH$ except as otherwise indicated.

DOW CORNING ® 190 was dimethicone copolyol from Dow Corning Corp. and was found to have a ratio of ethylene oxide units to propylene oxide units on the side chain of 2 5/1, and a number average molecular weight of 2570 and 9.1% silicon content: and was reported to have a viscosity was 1500 centistokes at 25° C. density 1.035, cloud point at 0.1% in water of 36° C. and the value of x was reported to be 3.

DOW CORNING ® 193 was dimethicone copolyol from Dow Corning Corp. was found to have 12.5% silicon and only contained ethylene oxide units on the side chain; and was reported to have a viscosity of 465 centistokes at 25° C., density of 1.07, a cloud point of 73° C. at 0.1% in water and the value of x was reported to be 3.

DOW CORNING ® 344 was octamethyl cyclotetrasiloxane from Dow Corning Corp. reported as octamethyl cyclotetrasiloxane and decamethyl cyclopentasiloxane, 90% (cyclomethicone).

DOW CORNING ® 345 was decamethyl cyclopentasiloxane and octamethyl cyclotetrasiloxane. 75% (cyclomethicone) from Dow Corning Corp.

DOW CORNING ® 02-5220 was dimethicone copolyol from Dow Corning Corporation which was found to have a silicon content of 5.4%, a number average molecular weight of 3102, and a ratio of ethyleneoxide units to propyleneoxide units of 2.5/1; and was reported to have a viscosity was 1000 centistokes at 25° C., density of 1.03, cloud point at 0.1% in water of 52° C. and the value of x was reported as 3.

ETHOMEEN 18/20 was polyoxyethylene (10) octadecylamine from AKZO Chemie America, ARMAK Chemicals, equiv. weight=705.

Hydrocarbon propellant A Was a mixture of 0.01% ethane, 15.90% propane. 35.57% iso-butane and 48.52% n-butane.

LEXAMINE L-13 was lauramidopropyl dimethylamine from Inolex Chemical Co. equiv. weight=287.

PVP K-90 Resin was a homopolymer of N-vinylpyrrolidone having a molecular weight of about 630,000 from GAF Corporation.

RESYN ® 28-2930 was a powdered carboxylated vinyl acetate terpolymer of vinyl acetate, crotonic acid and vinyl neodecanoate having 2% volatile content from National Starch and Chemical Corporation.

SILWET L-7602 was dimethicone copolyol from Union Carbide Corp. where the alkylene oxide containing siloxy units was believed to be $CH_3Si(C_3H_6)(OCH_2CH_2)_yOCH_3$ and was found to have 16% silicon content and a number average molecular weight of 1721 and was reported to have a viscosity of 70 to 130 centistokes. an average molecular weight of 3,000, density of 1.027, and cloud point at 1% in water was less that 10° C.

EXAMPLES 1-4

The following four hairspray compositions were prepared, charged in pressurized aerosol spray containers, and evaluated using a panel of 80 test subjects. The formulations used were as follows:

|  | Example No. | | | |
| --- | --- | --- | --- | --- |
|  | 1 | 2 | 3 | 4 |
| Acrylic Polymer A | 5.0 | 5.0 | 5.0 | 5.0 |
| ETHOMEEN 18/20 | 0.2 | 0.2 | — | — |
| AMP-95 | 0.3 | 0.3 | 0.3 | 0.3 |
| LEXAMINE L-13 | — | — | 0.2 | 0.2 |
| DOW CORNING Q2-5220 | 0.2 | — | 0.2 | — |
| SILWET L-7602 | — | 0.1 | — | 0.1 |
| DOW CORNING 345 | — | 0.1 | — | 0.1 |
| Absolute Ethanol | 64.15 | 64.15 | 64.15 | 64.15 |
| Fragrance | 0.15 | 0.15 | 0.15 | 0.15 |
| Hydrocarbon Propellant A | 30.00 | 30.00 | 30.00 | 30.00 |

-continued

|  | Example No. | | | |
|---|---|---|---|---|
|  | 1 | 2 | 3 | 4 |
|  | 100.00% | 100.00% | 100.00% | 100.00% |
| Knot Adhesion Value | 12.566 | 18.865 | 26.177 | 28.107 |
| Significance Level | B | B | A | A |
| Percent Neutr.[1] | 0 | 0 | 17.9 | 17.9 |
| Total Neutr.[2] | 44.3 | 44.3 | 53.9 | 53.9 |

[1] Percent of total carboxyl radicals neutralized, which were neutralized by LEXAMINE L-13.
[2] Percent of carboxy radicals neutralized by all amines present.

With regard to Knot Adhesion values, Examples 1 and 2 containing ETHOMEEN 18/20 were lower than the knot adhesion values observed for the LEXAMINE L-13. However, the knot adhesion value of a leading commercially available hairspray sold under the name "FINESSE" by Helene Curtis Industries, Inc. was evaluated and was found to a have a knot adhesion value of 17.451 grams with a significance level of B. Thus, the compositions of Examples 1 and 2 had knot adhesion values which were comparable to that of a leading hairspray formulation, FINESSE hairspray, and Examples 3–4 were better.

The purpose of the 80 member test panel was to determine what effects the amines and the silicones might have on the perceived performance of the hairspray compositions. The conclusion of the study was that parity performance was seen between the amines, with the exception that the LEXAMINE L-13 compositions were judged to have more resistance to blowing by the wind and a softer and less sticky feel than the compositions containing ETHOMEEN 18/20. The compositions containing the DOW CORNING Q2-5220 as a modifier were observed to have more beading a less wet spray were stickier and had less body 6 to 8 hours later than did the compositions containing SILWET L-7602 and DOW CORNING 345 Fluid. Thus, Example 4 appeared to have the most desirable properties for a hairspray compositions based on the 80 person panel test of these four formulations.

EXAMPLE 5

The following is an example of a composition which can be used in a self-pressurized aerosol hairspray product to obtain a hairspray composition exhibiting very good hold when sprayed on the hair.

|  | Example No. 5 |
|---|---|
| Acrylic Polymer B | 2.50 |
| Acrylic Polymer C | 1.25 |
| AMP-95 | 0.225 |
| LEXAMINE L-13 | 0.15 |
| SILWET L-7602 | 0.05 |
| DOW CORNING 345 | 0.05 |
| Fragrance | 0.05 |
| Absolute Ethanol | 60.725 |
| Isobutane | 35.0 |
|  | 100.00% |
| Percent Neutr.[1] | 17.9 |
| Total Neutr.[2] | 53.9 |

[1] Percent of total carboxyl radicals neutralized, which were neutralized by LEXAMINE L-13.
[2] Percent of carboxyl radicals neutralized by all amines present.

EXAMPLES 6–10

These Examples show the effect of silicone copolyols on the adhesion values as well as the use of LEXAMINE L-13 to improve the adhesion of hair spray compositions containing ULTRAHOLD 8 resin.

|  | Example No. | | | | |
|---|---|---|---|---|---|
|  | 6 | 7 | 8 | 9 | 10 |
| ULTRAHOLD 8 Resin | 2.0 | 2.0 | 2.0 | 2.0 | 2.0 |
| PVP K-90 Resin | 0.2 | 0.2 | 0.2 | 0.2 | 0.2 |
| AMP-95 | 0.2 | 0.135 | 0.135 | 0.135 | 0.135 |
| LEXAMINE L-13 | — | 0.2 | 0.2 | 0.2 | 0.2 |
| DOW CORNING Q2-5220 | 0.2 | 0.2 | 0.2 | — | — |
| SILWET L-7602 | — | — | — | 0.1 | 0.1 |
| DOW CORNING 345 | — | — | — | — | 0.1 |
| Benzyl alcohol | 0.2 | 0.2 | — | — | — |
| Absolute Ethanol | 47.15 | 47.015 | 47.215 | 47.315 | 47.215 |
| Fragrance | 0.05 | 0.05 | 0.05 | 0.05 | 0.05 |
|  | 50.00% | 50.00% | 50.00% | 50.00% | 50.00% |
| Knot Adhesion Test | 17.560 | 26.790 | 27.503 | 21.457 | 15.650 |
| Significance level | C | A,B | A | C,B | C |
| Percent Neutr.[1] | 0 | 32.7 | 32.7 | 32.7 | 32.7 |
| Total Neutr.[2] | 100 | 101 | 101 | 101 | 101 |

[1] Percent of carboxyl radicals neutralized by LEXAMINE L-13
[2] Percent of carboxyl radicals neutralized by all amines present.

The ULTRAHOLD 8 resin has a manufacturer's reported acid value of 58+5 and contains about 7.5% acrylic acid which calculates as 1.06 milliequivalents of carboxyl radical content per gram. Based on the above results, it can be seen from Examples 6 and 7 that the introduction of LEXAMINE L-13 improves the Knot Adhesion value of these hairspray compositions. The "Significance Level" indicates that values obtained for the Knot Adhesion Test which have significance levels of the same letter are comparable. Thus, the knot adhesion values for Examples 7 and 8 are statistically equivalent since both have significance levels of A. The compositions having a significance of level of C are statistically significantly different from those having significance levels of A or B.

The results also show that using differing types of silicones can affect the Knot Adhesion Value level. The higher silicone content of the SILWET L-7602 shows that it affects the adhesion values much more than does the DOW CORNING Q2-5220. Thus, less of the SILWET L-7602 should be used than is present in Examples 9 and 10 to optimize the Knot Adhesion values of these hairspray compositions.

EXAMPLES 11-22

In these examples, the Glass Slide Test was employed to evaluate the autophobic character of various silicone copolyols using the base (i.e., all but the propellant) hairspray formulation described in Example 1 of published European Patent Application No. 116.207 to Elliott et al. The base compositions were applied to the glass slides by quickly placing about 6 drops (about 0.2 milliliters) on the slide and spreading it to the edges of the slide with a plastic pipette. The resulting film was visually observed.

The base formulation used was

| | |
|---|---|
| ULTRAHOLD 8 | 1.2 g |
| AMP-95 | 0.1 g |
| Absolute Ethanol | 37.64 g |
| Silicones listed below | as below |

Example 11: Base plus 0.06 g DOW CORNING 193 and 1.00 g DOW CORNING 344. Result was a film that contracted toward the center of the slide very quickly. Upon complete drying, several cloudy, round puddles covering a total of about 10% of the area of the glass slide were observed.

Example 12: Base plus 0.06 g DOW CORNING 193 and 1.00 g DOW CORNING 345. Result was a film that contracted toward the center of the slide extremely quickly. Upon drying, several cloudy and flat puddles covering a total of about 15% of the area of the glass slide were observed.

Example 13: Base plus 0.06 SILWET L-7602 and 1.00 g DOW CORNING 345. Result was a film that contracted toward the center of the slide extremely quickly. Upon drying, several cloudy and flat puddles that were checked in appearance and covering a total of about 10% of the area of the glass slide were observed.

Example 14: Base plus 0.06 g DOW CORNING Q2-5220 and 1.00 g DOW CORNING 345. Result was a film that contracted toward the center of the slide extremely quickly. Upon drying, one cloudy and flat puddle that was slightly checked in appearance and covering about 10% of the area of the glass slide was observed.

Example 15: Base plus 0.2 g DOW CORNING Q2-5220. Result was a smooth uniform clear film which covered the entire area of the slide and had a few slight ridges at the edges of the slide after drying.

Example 16: Base plus 0.2 g SILWET L-7602. Result was a film which contracted towards the center of the slide upon drying to leave 3 dry, long and narrow films at the center of the slide occupying a total of about 15% of the area of the glass slide. The puddles had a clear to slightly hazy appearance.

Example 17: Base plus 1.0 g DOW CORNING 344. Result was a film which contracted towards the center of the slide upon drying to leave a dry, puddled film at the center of the slide occupying about 10% of the area of the glass slide. The puddle was cloudy in appearance.

Example 18: Base plus 1.0 g DOW CORNING 345. Result was a film which contracted towards the center of the slide upon drying to leave a dry, large and wide film at the center of the slide occupying about 25% of the area of the glass slide. The puddle was cloudy in appearance.

Example 19: Base plus 0.06% SILWET L-7602 and 0.06% DOW CORNING 345. Result was a film which contracted towards the center of the slide upon drying to leave two dry puddles at the center of the slide occupying a total of about 10% of the area of the glass slide. The puddles were slightly hazy in appearance.

Example 20: Base only, no silicone material. Result was a film which remained evenly spread across the slide and dried to form a very smooth clear film.

Example 21: Base plus 0.2 g DOW CORNING 193. Result was a film which remained evenly spread across the film during drying. Upon drying, a ridge was observed to form close to the edge of the edges of the glass slide as if a slight contraction had taken place, but the dried film occupied a total of about 100% of the area of the slide. The film was slightly hazy.

Example 22: Base plus 0.2 g DOW CORNING Q4-3667. Result was a film that contracted extremely rapidly upon drying. After drying, the film was one large and elongated puddle occupying about 35% of the area of the slide. The dried film was slightly hazy.

A commercial sample of hairspray composition sold by Helene Curtis Industries, Inc. under the tradename FINESSE was sprayed on a glass slide and was observed to have about the same film characteristics reported for Example 11, except that the film was more elongated like that observed for Example 16. The container label for the FINESSE hairspray listed dimethicone copolyol and cyclomethicone as ingredients.

From the above, only the SILWET L-7602 (Example 16) was capable of imparting autophobic properties to the hairspray composition by itself. The silicone copolyols alone used in Examples 15 and 21 did not render the normally non-autophobic hairspray composition (Example 20 with no silicone) autophobic. The addition of DOW CORNING 344 or 345 which are hydrophobic cyclomethicones imparted an autophobic property to the compositions containing DOW CORNING Q2-5220 and 193. The addition of DOW CORNING 345 to the composition containing SILWET L-7602 appeared to enhance the rate of contraction of the film in Example 13.

The Knot Adhesion values of Examples 11 to 20 were evaluated, but the results were not deemed to be statistically reliable because, at best, only one composition (Example 15) had 11 of the 20 hair strands tested which gave measurable adhesion values and the others had considerably less than 11 strands which gave measurable adhesion values.

EXAMPLES 23-26

These Examples were based on the propellant-free portion of the formulations (parts by weight) given in Example 2 of the Elliott et al. European Application No. 116,207 noted above to check on the poor knot adhesion test results obtained in Examples 11-20. The knot adhesion values of the compositions were evaluated as well as the Glass Slide Test results for the following compositions:

| | Example No. | | | |
|---|---|---|---|---|
| | 23 | 24 | 25 | 26 |
| RESYN ® 28-2930 | 1.8 | 1.8 | 1.8 | 1.8 |
| AMP-95 | 0.17 | 0.17 | 0.17 | 0.17 |
| DOW CORNING 193 | 0.1 | — | — | 0.2 |
| SILWET L-7602 | — | 0.1 | 0.2 | — |
| DOW CORNING 345 | 1.0 | 1.0 | — | — |
| Absolute Ethanol | 36.93 | 36.93 | 36.93 | 36.93 |
| Knot Adhesion Value | 28.858 | 21.937 | 19.666 | 30.109 |

-continued

| | Example No. | | | |
|---|---|---|---|---|
| | 23 | 24 | 25 | 26 |
| Significance Level | A | B | B | A |

Unlike Examples 11-20, knot adhesion values were obtained for every one of the 20 hair strands run for each of Examples 23-26. The Knot Adhesion test results showed that the samples containing DOW CORNING 193 had a statistically significantly higher amount of knot adhesion (significance level A) versus those containing SILWET L-7602 (significance level B). Thus, Examples 23 and 26 were comparable in adhesion while Examples 24 and 25 were also comparable in adhesion. The data appears to show that the SILWET L-7602 has more silicone character than (i.e.. the resin does not hold the hair fibers as tightly as) does the DOW CORNING 193 and thus a product with less adhesion is produced at the same level of silicone copolyol content. It indicates that for this formulation, a lesser amount of SILWET L-7602 would be indicated in view of the lower adhesion values observed.

The Glass Slide Test was run for these Examples in the same manner as described for Examples 11-22. The results were as follows:

Example 23: The dried film was composed of a single round puddle which was hazy in appearance and occupied about 15% of the surface area of the glass slide.

Example 24: The dried film was composed of two somewhat elongated puddles which were hazy in appearance and occupied a total of about 15% of the surface area of the glass slide.

Example 25: The dried film was composed of several narrow and elongated puddles which were clear in appearance and occupied a total of about 15% of the surface area of the glass slide.

Example 26: The dried film was clear and uniformly coated over the entire area of the slide and had a slight raised ridge near the edges of the slide.

Thus, Examples 23 and 24 with the cyclic polydimethylsiloxanes were autophobic as was Example 25 with only the autophobic SILWET L-7602 while Example 26 was not autophobic. The addition of the cyclic polydimethylsiloxanes apparently caused a haze to develop in the dried films since the samples containing only the silicone copolyols were both clear.

EXAMPLES 27-32

In these Examples, various other commercially available silicone copolyols which are sold by Union Carbide Corporation under the tradename "SILWET" were evaluated using the Glass Slide Test. An intermediate hairspray composition was prepared using the following formulation: 25 parts of Acrylic polymer D, 1.5 parts of AMP-95, 1.0 parts of LEXAMINE L-13 and 72.5 parts Absolute Ethanol (hereinafter referred to as "Intermediate"). Examples 27-32 were then prepared having the following compositions. The characteristics of each of the silicone copolyols used are listed below under the Example number in which the silicone copolyol is used. All of the silicone copolyols were stated as being Dimethicone Copolyols.

| | Example No. | | | | |
|---|---|---|---|---|---|
| | 27 | 28 | 29 | 30 | 31 |
| Intermediate | 8.0 | 8.0 | 8.0 | 8.0 | 8.0 |
| SILWET L-77 | 0.1 | — | — | — | — |
| SILWET L-7600 | — | 0.1 | — | — | — |
| SILWET L-7604 | — | — | 0.1 | — | — |
| SILWET L-7607 | — | — | — | 0.1 | — |
| SILWET L-7614 | — | — | — | — | 0.1 |
| Fragrance | 0.15 | 0.15 | 0.15 | 0.15 | 0.15 |
| Absolute Ethanol | 56.75 | 56.75 | 56.75 | 56.75 | 56.75 |
| Isobutane | 35.0 | 35.0 | 35.0 | 35.0 | 35.0 |
| | 100.00% | 100.00% | 100.00% | 100.00% | 100.00% |
| Silicone Characteristics[1] | | | | | |
| Cloud Point | [2] | 64 | 50 | 58 | 88 |
| Viscosity(cSt) | 20 | 110 | 420 | 50 | 480 |
| Density | 1.007 | 1.066 | 1.063 | 1.050 | 1.084 |
| Molecular Wt. | 600 | 4,000 | 4,000 | 1,000 | 5,000 |
| Polyether Type | EO/MT | EO/MT | EO/OH | EO/MT | EO/OH |

[1] As reported by the manufacturer Cloud Point of 1% solution in water in degrees C.
EO/OH = polyethylene oxide only in pendant sidechain, hydroxyl radical at end of polyether chain.
EO/MT = polyethylene oxide only in pendant sidechain, methoxy radical at end of polyether chain.
[2] Reported to be dispersible in water at 1% w/w but already hazy; Cloud Point of 0.1% solution is <10° C.

All of the above compositions gave uniform films that did not contract towards the center of the glass slide during the Glass Slide Test. The dry film of Example 27 appeared to have a more lubricated surface than any of the other dried films. Thus, none of these silicone copolyols rendered the compositions autophobic in spite of the diversity of molecular weight and properties and demonstrates the uniqueness of the SILWET L-7602 silicone copolyol.

That which is claimed is:

1. An aerosol hairspray composition having improved body consisting essentially of from 0.5% to 8.0% by weight of an ethanol soluble hairspray resin dissolved in a sufficient amount of an ethanol solvent system to render the composition sprayable in aerosol form, said composition further containing an effective amount of an autophobic silicone copolyol to cause the sprayed film to contract on the hair at between 20° C. to 37° C. rather than to spread into an even film upon drying, said silicone copolyol consisting essentially of organosiloxy units selected from the group consisting of dimethylsiloxy units, $CH_3SiO(C_xH_{2x})(OCH_2CH_2)_y(OCHCH_3CH_2)_zOR$, $(CH_3)_2SiO(C_xH_{2x})(OCH_2CH_2)_y(OCHCH_3CH_2)_zOR$, and trimethylsiloxy units, and having a number average molecular weight of about 1500 to 6000 wherein x has a value of from 1 to 12, R is hydrogen or alkyl of 1 to 4 carbon atoms, y is greater than or equal to 1 and z is greater than or equal to 0 and the sum of y+z and the amount of dimethylsiloxy units and trimethylsiloxy units present is such that the silicone copolyol causes an ethanolic solution of the hairspray resin to contract on the hair rather to spread into an even film at 20° C. to 37° C. upon drying and a 0.1% by weight solution of the silicone copolyol in water has a cloud point of less than 30° C. and said ethanol solvent system consists essentially of at least 70% by weight of ethanol and any remaining solvent is selected from the group consisting of water. $R^1OH$ where $R^1$ is an alkyl of 3 or 4 carbon atoms, and mixtures thereof.

2. The composition as claimed in claim 1 wherein the silicone copolyol is present in an amount of from about 0.02% to 0.5% by weight of the composition.

3. The composition as claimed in claim 1 wherein the silicone copolyol is composed of dimethylsiloxane units, $CH_3SiO(C_3H_6)(OCH_2CH_2)_yOCH_3$ units endblocked with trimethylsiloxy units, has a silicon content of about 16% by weight, a number average molecular weight of about 1700, a density of 1.027 and a viscosity at 25° C. of from about 70 to 130 centistokes, z is 0 and R is methyl.

4. The composition as claimed in claim 1 wherein the composition further contains a cyclic silicone fluid of the formula $[(CH_3)_2SiO]_n$ where n has an average value of about 4 to about 5 wherein the total mount of silicone copolyol and cyclic silicone fluid is from about 0.02% to about 0.5 weight percent based on the total weight of the composition.

5. The composition as claimed in claim 1 wherein the average value of y is at least 5.

6. The composition as claimed in claim 4 wherein the silicone copolyol is composed of dimethylsiloxane units and $CH_3SiO(C_3H_6)(OCH_2CH_2)_yOCH_3$ units endblocked with trimethylsiloxy units, has a silicon content of about 16% by weight, a number average molecular weight of about 1700, a density of 1.027 and a viscosity at 25° C. of from about 70 to 130 centistokes.

7. The composition as claimed in claim 1 wherein from about 10 to 80% based on the total weight of the composition is an aerosol propellant and the resin is from 0.5% to 6% of the composition.

8. The composition as claimed in claim 1 wherein the cloud point of the silicone copolyol is no more than about 10° C.

9. The composition as claimed in claim 1 wherein the composition further contains a silicone fluid of the formula $(CH_3)_3SiO[(CH_3)_2SiO]_qSi(CH_3)_3$ where q has an average value such that the viscosity of the silicone fluid is no more than about 20 centistokes at 25° C. wherein the total amount of silicone copolyol and silicone fluid is from about 0.02% to about 0.5% weight percent based on the total weight of the composition.

10. The composition as claimed in claim 9 wherein the viscosity of said silicone fluid is no more than about 10 centistokes at 25° C.

11. The composition as claimed in claim 1 wherein the amount of said silicone copolyol is in the range of from about 0.05% to 0.2% by weight based on the total weight of the composition.

12. The composition as claimed in claim 4 wherein the total amount of silicone copolyol and cyclic silicone fluid is about 0.1% to 0.2% of the total weight of the composition 13. The composition as claimed in claim 4 wherein the weight ratio of silicone copolyol to cyclic silicone fluid is about 1:1.

14. The composition as claimed in claim 10 wherein the total amount of silicone copolyol and the silicone fluid is about 0.1 to 0.2% of the total weight of the composition.

15. The composition as claimed in claim 10 wherein the weight ratio of silicone copolyol to silicone fluid is about 1:1.

16. The composition as claimed in claim 1 wherein the silicone copolyol has an average of about 10 dimethylsiloxy units and is endblocked with $(CH_3)_2Si(C_3H_6)(OCH_2CH_2)_xOH$ units where the total value of x in the endblocking units has an average value of about 26.

17. The composition as claimed in claim 16 wherein the amount of said silicone copolyol is in the range of 0.1 to 0.2% of the total weight of the composition.

18. The composition as claimed in claim 1 wherein the silicone copolyol contains at least 10% silicon content.

19. An aerosol hairspray composition having improved body consisting essentially of from 0.5% to 8.0% by weight of an ethanol soluble hairspray resin dissolved in a sufficient amount of an ethanol solvent system to render the composition sprayable in aerosol form, said composition further containing from about 0.02 to 0.5% by weight of an autophobic silicone copolyol, said amount being sufficient to cause the sprayed film to contract on the hair at between 20° C. to 37° C. rather than to spread into an even film upon drying, said silicone copolyol consisting essentially of organosiloxy units selected from the group consisting of dimethylsiloxy units, $CH_3SiO(C_xH_{2x})(OCH_2CH_2)_yOR$, and trimethylsiloxy units, and having a silicon content of at least 10 percent by weight and a number average molecular weight of about 1500 to 6000 wherein x has a value of from 3 to 4, R is hydrogen or alkyl of 1 to 4 carbon atoms, y is at least 5 and the value of y and the amount of dimethylsiloxy units and trimethylsiloxy units present is such that the silicone copolyol causes an ethanolic solution of the hairspray resin to contract on the hair rather to spread into an even film at 20° C. to 37° C. upon drying and a 0.1% by weight solution of the silicone copolyol in water has a cloud point of less than 30° C. and said ethanol solvent system consists essentially of at least 70% by weight of ethanol and any remaining solvent is selected from the group consisting of water $R^1OH$ where $R^1$ is an alkyl of 3 or 4 carbon atoms, and mixtures thereof.

20. The composition as claimed in claim 19 wherein the silicone copolyol has a silicon content of between about 15 and 30 percent and the cloud point is less than 10° C.

21. The composition as claimed in claim 20 wherein the composition further contains a cyclic silicone fluid of the formula $[(CH_3)_2SiO]_n$ where n has an average value of about 4 to about 5 wherein the total mount of silicone copolyol and cyclic silicone fluid is from about 0.02% to about 0.5 weight percent based on the total weight of the composition.

22. The composition as claimed in claim 21 wherein the silicone copolyol has a silicon content of about 16% by weight, a number average molecular weight of about 1700, a density of 1.027 and a viscosity at 25° C. of from about 70 to 130 centistokes, and R is methyl.

23. The composition as claimed in claim 20 wherein the composition further contains a silicone fluid of the formula $(CH_3)_3SiO[(CH_3)_2SiO]_qSi(CH_3)_3$ where q has an average value such the viscosity of the silicone fluid is no more than about 20 centistokes at 25° C. wherein the total amount of silicone copolyol and silicone fluid is from about 0.02% to about 0.5% weight percent based on the total weight of the composition.

* * * * *

UNITED STATES PATENT AND TRADEMARK OFFICE
CERTIFICATE OF CORRECTION

PATENT NO. : 4,871,529

DATED : October 3, 1989

INVENTOR(S) : John A. Sramek

It is certified that error appears in the above-identified patent and that said Letters Patent is hereby corrected as shown below:

In line 1 of the Abstract, the word "in" should be --is--.

In line 9 of the Abstract, the formula ")$(OCH_2CH_2)_y(OCHCH_3CH_2)_zOR$--. should be --)$(OCH_2CH_2)y(OCHCH_3CH_2)_zOR$--.

In line 12 of the Abstract, the word "carboxy" should be --carbon--.

In column 19, line 11, "water." should be --water,--.

In column 20, line 42, "water" should be --water,--.

Signed and Sealed this

Tenth Day of March, 1992

Attest:

HARRY F. MANBECK, JR.

*Attesting Officer*  *Commissioner of Patents and Trademarks*